US011382894B2

(12) United States Patent
Bellien et al.

(10) Patent No.: US 11,382,894 B2
(45) Date of Patent: Jul. 12, 2022

(54) PHARMACEUTICAL COMPOSITIONS FOR USE IN THE TREATMENT OF CARDIOVASCULAR CALCIFICATION

(71) Applicants: INSERM (INSTITUT NATIONAL DE LA SANTE ET DE LA RECHERCHE MEDICALE), Paris (FR); UNIVERSITE DE ROUEN NORMANDIE, Mont-Saint-Aignan (FR); UNIVERSITE DE PICARDIE JULES VERNE, Amiens (FR); CENTRE HOSPITALIER UNIVERSITAIRE DE ROUEN, Rouen (FR); CENTRE HOSPITALIER UNIVERSITAIRE D'AMIENS, Amiens (FR)

(72) Inventors: Jeremy Bellien, Rouen (FR); Isabelle Six, Amiens (FR); Romuald Mentaverri, Amiens (FR); Said Kamel, Amiens (FR)

(73) Assignees: INSERM (INSTITUT NATIONAL DE LA SANTE ET DE LA RECHERCHE MEDICALE), Paris (FR); UNIVERSITE DE ROUEN NORMANDIE, Rouen (FR); UNIVERSITE DE PICARDIE JULES VERNE, Amiens (FR); CENTRE HOSPITALIER UNIVERSITAIRE DE ROUEN, Rouen (FR); CENTRE HOSPITALIER UNIVERSITAIRE D'AMIENS, Amiens (FR)

( * ) Notice: Subject to any disclaimer, the term of this patent is extended or adjusted under 35 U.S.C. 154(b) by 252 days.

(21) Appl. No.: 16/498,807

(22) PCT Filed: Mar. 29, 2018

(86) PCT No.: PCT/EP2018/058115
§ 371 (c)(1),
(2) Date: Sep. 27, 2019

(87) PCT Pub. No.: WO2018/178253
PCT Pub. Date: Oct. 4, 2018

(65) Prior Publication Data
US 2021/0113527 A1 Apr. 22, 2021

(30) Foreign Application Priority Data

Mar. 30, 2017 (EP) .................................... 17305370
Nov. 10, 2017 (EP) .................................... 17306561

(51) Int. Cl.
*A61K 31/41* (2006.01)
*A61P 9/10* (2006.01)
*A61K 31/198* (2006.01)
*C12Q 1/42* (2006.01)

(52) U.S. Cl.
CPC ............ *A61K 31/41* (2013.01); *A61K 31/198* (2013.01); *A61P 9/10* (2018.01); *C12Q 1/42* (2013.01); *G01N 2800/32* (2013.01)

(58) Field of Classification Search
None
See application file for complete search history.

(56) References Cited

U.S. PATENT DOCUMENTS

2009/0069418 A1  3/2009  Alkayed et al.
2015/0306281 A1  10/2015  Rajamannan

FOREIGN PATENT DOCUMENTS

| WO | 2001/049295 A1 | 7/2001 | |
| WO | WO 01/049295 A1 * | 12/2001 | |
| WO | 2010/025043 A1 | 3/2010 | |
| WO | 2016/033150 A1 | 3/2016 | |
| WO | WO-2016033150 A1 * | 3/2016 | ........... C07D 401/12 |
| WO | 2017/064171 A1 | 4/2017 | |

OTHER PUBLICATIONS

Liu et al. "Current understanding of coronary artery calcification," Journal of Geriatric Cardiology (2015) 12: 668-675 (Year: 2015).*
FDA Guidance for Industry "FDA Guidance", Oct. 2011 Labeling. (Year: 2011).*
Klingler et al. "Bacterial Expression and HTS Assessment of Soluble Epoxide Hydrolase Phosphatase," Journal of Biomolecular Screening 21(7) 689-694. (Year: 2016).*
Enayetallah et al: "Effects of human soluble epoxide hydrolase polymorphisms on isoprenoid phosphate hydrolysis", Biochemical and Biophysical Research Communications, Elsevier, Amsterdam, NL, vol. 341, No. 1, pp. 254-260, Mar. 3, 2006.
Chew et al: "Site-Specific Antiatherogenic Effect of the Antioxidant Ebselen in the Diabetic Apolipoprotein E-Deficient Mouse", Arteriosclerosis, Thrombosis, and Vascular Biology., vol. 29, No. 6, p. 823-830, Jun. 1, 2009.
Varennes et al: "Opposite roles of the soluble epoxide hydrolase domains in the development of vascular calcification", Circulation Nov. 1, 2017 Lippincott Villiams and Wilkins NLD, vol. 136, Nov. 1, 2017.

* cited by examiner

*Primary Examiner* — Jeffrey S Lundgren
*Assistant Examiner* — Michael J Schmitt
(74) *Attorney, Agent, or Firm* — WC&F IP

(57) ABSTRACT

The inventors demonstrate that the phosphatase and hydrolase domains of soluble epoxide hydrolase (sEH) regulate the cardiovascular calcification process and revealed that inhibition of the phosphatase domain of sEH could represent a new pharmacological target in the prevention of cardiovascular calcification. The present invention thus relates to a therapeutically effective amount of an inhibitor of phosphatase activity of soluble epoxide hydrolase for use in a method of treating cardiovascular calcification in a subject in need thereof.

5 Claims, 4 Drawing Sheets

Figure 1:
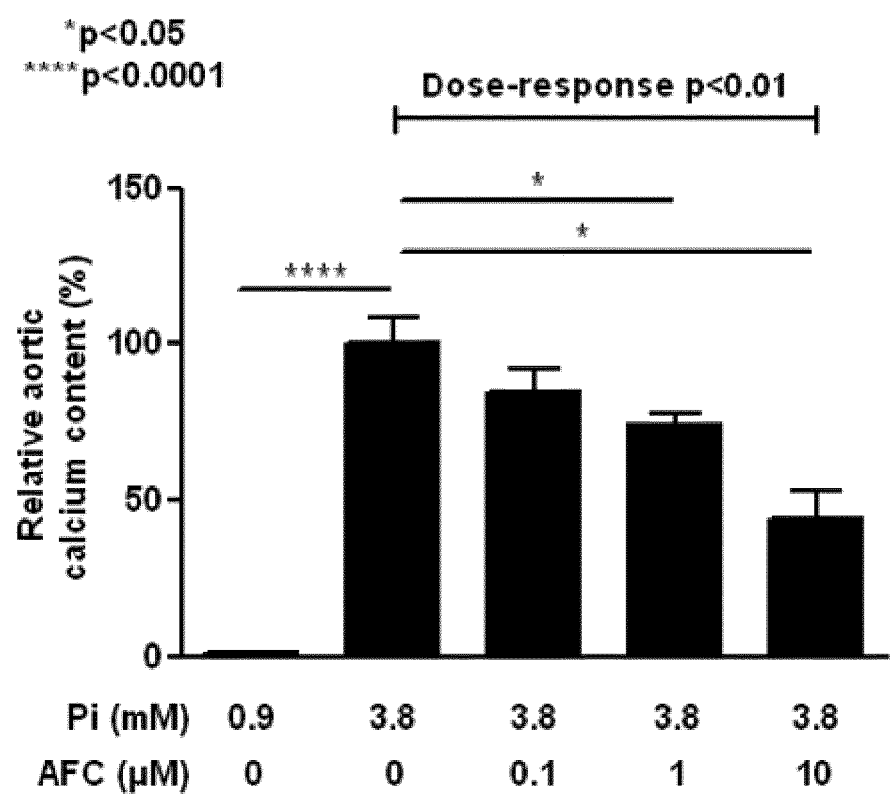

PHARMACEUTICAL COMPOSITIONS FOR USE IN THE TREATMENT OF CARDIOVASCULAR CALCIFICATION

FIELD OF THE INVENTION

The present invention relates to methods and pharmaceutical compositions for the treatment of cardiovascular calcification using inhibitors of the phosphatase domain of soluble epoxide hydrolase.

BACKGROUND OF THE INVENTION

Cardiovascular calcification, a prominent feature of chronic inflammatory disorders such as chronic renal disease, type II diabetes and dyslipidemia, associates with significant morbidity and mortality. Cardiovascular calcification is an active, cell-regulated process in which vascular smooth muscle cells (SMCs) and/valvular interstitial cells (VICs) can lose the expression of their marker genes, acquire osteogenic markers, and deposit a mineralized bone-like matrix. SMCs and VICs play an important role in this process via transition toward an osteoblast-like state and/or releasing calcified matrix vesicles and microparticles. Calcification in coronary arteries promotes heart attacks, which represent major health problems and economic burden in the United States. Calcification in carotid arteries associate with risk for stroke and dementia. Calcification in aortic valves causes aortic stenosis and heart failure. An increased burden of vascular and valvular calcification is observed due to the growing of older population. Especially, patients with mineral imbalance and calcium/phosphate disorders, including chronic renal disease, hemodyalysis and type II diabetes suffer from accelerated vascular and valvular calcification. For instance, arteriovenous shunts/grafts for hemodialysis in patients with chronic renal disease, vein grafts for peripheral arterial disease in diabetic patients, and saphenous vein bypass grafts for occluded coronary arteries in patients with metabolic disorders are often occluded within a year (vein graft failure). Various therapeutic agents have been investigated to target cardiovascular calcification; these include statins (Aikawa E et al, Circulation, 2007; Monzack E L et al, Atheroscler Thromb Vasc Biol, 2009; Osman L et al, Circulation, 2006; Rajamannan N M et al, Circulation, 2005; Wu Y W et al, Eur J Nucl Med Mol Imaging, 2012), bisphosphonate (Hartle J E et al, Am J Kidney Dis, 2012), phosphate binder (Di Iorio B et al, Clin J Am Soc Nephrol, 2012) and mineralocorticoid receptor antagonists (Gkizas S et al, Cardiovasc Pharma, 2010; Jaffe I Z et al, Atheroscler Thromb Vasc Biol, 2007). However, beneficial effects of these drugs remain uncertain in the clinical setting (Gilmanov D, Interact Cardiovasc Thor Surg, 2010). Thus, despite global clinical burden of cardiovascular calcification, no medical therapies are available.

Notably expressed in the cardiovascular system either by endothelial, vascular smooth muscle and cardiac cells, soluble epoxide hydrolase (sEH) is a bifunctional enzyme which contributes to the regulation endothelial function and maintain of cardiovascular homeostasis. Aside from its hydrolase activity, sEH also possesses a phosphatase domain whose function has been poorly investigated. Two clinical studies show that the presence of some polymorphisms of the soluble epoxide hydrolase gene EPHX2, which increase sEH hydrolase activity but may also affect its phosphatase activity is associated with arterial calcification in African-American or European-American subjects (Fornage M et al, Circulation. 2004; 109:335-339; Burton K P et al, DiabVasc Dis Res, 2008). Following this, the enhanced cardiovascular calcification could be related to a procalcifying effect of sEH phosphatase.

SUMMARY OF THE INVENTION

The present invention relates to methods and pharmaceutical compositions for the treatment of cardiovascular calcification. In particular, the present invention is defined by the claims.

DETAILED DESCRIPTION OF THE INVENTION

The inventors assessed the role of the sEH hydrolase and phosphatase domains in cardiovascular calcification. They demonstrated that the phosphatase and hydrolase domains of sEH regulate the cardiovascular calcification process and unexpectedly revealed that inhibition of the phosphatase domain of sEH could represent a new pharmacological target in the prevention of cardiovascular calcification.

Accordingly, the first object of the present invention relates to a method of treating cardiovascular calcification in a subject in need thereof comprising administering to the subject a therapeutically effective amount of an inhibitor of phosphatase activity of soluble epoxide hydrolase.

As used herein, the term "cardiovascular calcification" has its general meaning in the art and refers to formation, growth or deposition of extracellular matrix hydroxyapatite (calcium phosphate) crystal deposits in cardiovascular tissues. The term encompasses vascular and valvular calcification and more particularly encompasses coronary, aortic, arterial, vein graft, tissue-engineered vessel, and other blood vessel calcification as well as aortic valve and mitral annulus calcification. The term includes atherosclerotic and medial wall calcification in vessels.

The method of the present invention is particularly suitable to treat atherosclerotic calcification, medial calcification, aortic valve calcification, and other conditions characterized by cardiovascular calcification. For example, the method of the present invention can be used to treat cardiovascular calcification in elderly subjects and in patients with any mineral imbalance disorders, including severe renal failure on hemodialysis, hemodialysis AV grafts/shunts, vein grafts, various vascular anastomosis, diabetes, Paget's disease, rheumatoid arthritis, osteoporosis or some forms of osteoarthritis. In some embodiments, cardiovascular calcification can be associated with chronic renal insufficiency or end-stage renal disease. In some embodiments, cardiovascular calcification can be associated with pre- or post-dialysis or uremia. In some embodiments, cardiovascular calcification can be associated with type I or II diabetes. In some embodiments, cardiovascular calcification can be associated with a cardiovascular disorder. In some embodiments, cardiovascular calcification can be associated with bone disease (Paget's disease, rheumatoid arthritis, osteoporosis, osteoarthritis). Accordingly, in some embodiments, the subject has chronic renal disease, severe renal failure treated with hemodialysis, hemodialysis AV grafts/shunts, vein grafts, vascular anastomosis, Paget's disease, diabetes, dyslipidemia, osteoarthritis, rheumatoid arthritis or osteoporosis. In some embodiments, the subject has a transcatheter valve implant.

Methods of detecting and measuring cardiovascular calcification are well known in the art. Typically the methods include but are not limited to in vivo imaging methods such as plain film roentgenography, coronary arteriography; fluoroscopy, including digital subtraction fluoroscopy; cinefluorography; conventional, helical, and electron beam computed tomography; intravascular ultrasound (NUS); magnetic resonance imaging; and transthoracic and transesophageal echocardiography. Fluoroscopy and EBCT are most commonly used to detect calcification noninvasively, while cinefluorography and IVUS are used by coronary interventionalists to evaluate calcification in specific lesions before angioplasty. Transthoracic echocardiography is commonly used to detect aortic valve calcification.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "soluble epoxide hydrolase" or "sEH" has its general meaning in the art and refers to the ubiquitous enzyme encodes by the EPXH2 gene. The cloning, sequence, and accession numbers of the human sEH sequence are set forth in Beetham et al, Arch. Biochem. Biophys. 305(1):197-201 (1993). The amino acid sequence of human sEH is disclosed in U.S. Pat. No. 5,445,956.

As used herein, the term "inhibitor" includes drugs for inhibiting activity of the targeted molecule. The mode of the inhibitor is not particularly limited, and examples include e.g. low-molecular compounds, antibodies and aptamer. As used herein, the expression "inhibitor of phosphatase activity of soluble epoxide hydrolase" refers to any dug capable of inhibiting the phosphatase activity of the enzyme without inhibiting or enhancing its hydrolase activity. Typically, the inhibitors are ligands for the amino terminus active site associated with the phosphatase activity of the enzyme. In some embodiments, the inhibitor of the present invention is a competitive inhibitor which allosterically alter the phosphatase activity of the enzyme. In some embodiments, the inhibitor of the present invention is non-competitive inhibitor which alter the phosphatase activity of the enzyme by modifying its configuration Assays for determining whether a compound would inhibit phosphatase activity of soluble epoxide hydrolase are well known in the art and typically include the methods disclosed in:

Enayetallah A E, Grant D F. Effects of human soluble epoxide hydrolase polymorphisms on isoprenoid phosphate hydrolysis. BiochemBiophys Res Commun. 2006 Mar. 3; 341(1):254-60.

Cronin A, Homburg S, Dürk H, Richter I, Adamska M, Frère F, Arand M. Insights into the catalytic mechanism of human sEH phosphatase by site-directed mutagenesis and LC-MS/MS analysis. J Mol Biol. 2008 Nov. 14; 383(3): 627-40.

Hahn S, Achenbach J, Buscató E, Klingler F M, Schroeder M, Meirer K, Hieke M, Heering J, Barbosa-Sicard E, Loehr F, Fleming I, Doetsch V, Schubert-Zsilavecz M, Steinhilber D, Proschak E. Complementary screening techniques yielded fragments that inhibit the phosphatase activity of soluble epoxide hydrolase. ChemMedChem. 2011 Dec. 9; 6(12):2146-9.

Morisseau C, Sandeo S, Cortopassi G, Hammock B D. Development of an HTS assay for EPHX2 phosphatase activity and screening of nontargeted libraries. Anal Biochem. 2013 Mar. 1; 434(1):105-11. doi: 10.1016/j.ab.2012.11.017.

Klingler F M, Wolf M, Wittmann S, Gribbon P, Proschak E. Bacterial Expression and HTS Assessment of Soluble Epoxide Hydrolase Phosphatase. J Biomol Screen. 2016 August; 21(7):689-94.

Exemplary inhibitors of phosphatase activity of sEH includes the compounds disclosed in the International Patent Application WO2007022059. In some embodiments, the inhibitor of the present invention is selected from the group consisting of compounds with the structure set forth below:

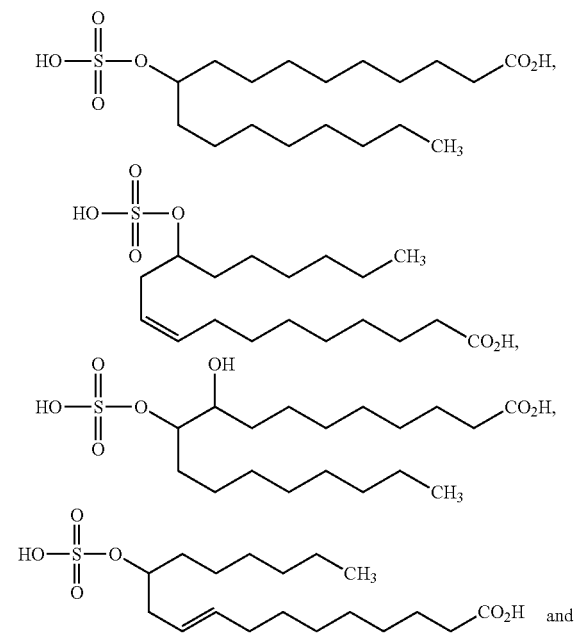

and

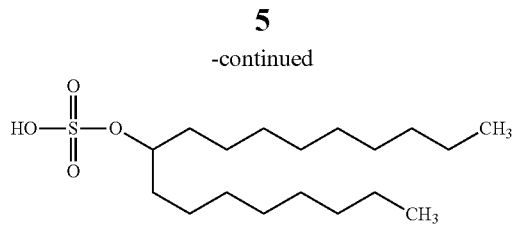

In some embodiments the inhibitor of phosphatase activity of sEH can correspond to ebselen, disclosed in the article untitled "Development of an HTS assay for EPHX2 phosphatase activity and screening of nontargeted libraries" and published in Analytical Biochemistry, with the structure set forth below:

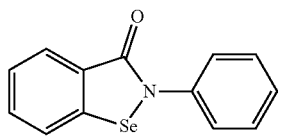 [SMILES: O=c1c2ccccc2[se]n1-c1ccccc1]

Other exemplary inhibitors of phosphatase activity of sEH includes the compounds disclosed in the communication untitled "Complementary Screening Techniques Yielded Fragments that Inhibit the Phosphatase Activity of Soluble Epoxide Hydrolase" and published in ChemMedChem. In some embodiments, the inhibitor of the present invention is selected from the group consisting of compounds with the structure set forth below:

Screening round 1

1

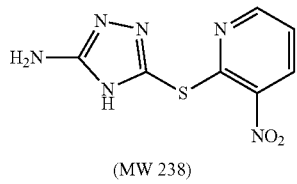

(MW 238)

2

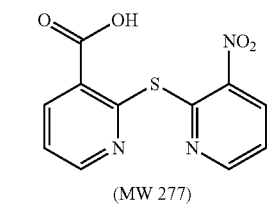

(MW 242)

Screening round 2

3

(MW 277)

4

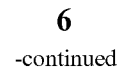

(MW 175)

5

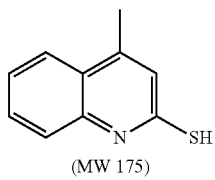

(MW 214)

Some more examples of inhibitors of sEH phosphatase activity are disclosed in the article untitled "Bacterial Expression and HTS Assessment of Soluble Epoxide Hydrolase Phosphatase" and published in Journal of Biomolecular Screening. In some embodiments, the inhibitor of the present invention is selected from the group consisting of the following compounds Entacapone, Tolacapone, Oxaprozin, Silver sulfadiazine and Tiludronic acid.

By a "therapeutically effective amount" is meant a sufficient amount of the inhibitor of the present invention for treating cardiovascular calcification at reasonable benefit/risk ratio. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination with the inhibitor of the present inventions; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250, 500 and 1,000 mg of the inhibitor of the present invention for the symptomatic adjustment of the dosage to the subject to be treated.

In some embodiments, the inhibitor of the present invention may be administered alone or in combination with other drugs for treating cardiovascular calcification, such as vitamin D sterols and/or calcium acetate or carbonate and/or phosphate binders. Vitamin D sterols can include calcitriol, alfacalcidol, doxercalciferol, maxacalcitol or paricalcitol. Phosphate binders can include sevelamer, lanthanum carbonate or sucroferricoxyhydroxide In some embodiments, the inhibitor can be administered before or after administration of vitamin D sterols, calcium acetate or carbonate and/or phosphate binders. In some embodiments, the inhibitors can be co-administered with vitamin D sterols, calcium acetate or carbonate and/or phosphate binders. Typically the inhibitor of the present invention is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In the pharmaceutical compositions of the present invention, the inhibitor of the present inventions of the invention can be administered in a unit administration form, as a mixture with conventional pharmaceutical supports. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

A further object of the present invention relates to a method for screening a plurality of test substances useful for the treatment of cardiovascular calcification in a subject in need thereof comprising the steps consisting of i) testing each of the test substances for its ability to inhibit the phosphatase activity of soluble epoxide hydrolase and ii) identifying the test substance which inhibits said activity thereby to identify a test substance useful for treating cardiovascular calcification in a subject in need thereof.

Any assay well known in the art may be used for testing the ability of test substance to inhibit phosphatase activity of sEH and typically include the assays described in Enayetallah 2006; Cronin 2008; Hahn 2011; Klingler 2016, Morisseau 2013 as above described.

A variety of cells may be used in the in vitro assays. In some embodiments, a broad variety of host-expression vector systems may be utilized to express sEH in a cell of interest. These include, but are not limited to, mammalian cell systems such as human cell lines. The mammalian cell systems may harbour recombinant expression constructs containing promoters derived from the genome of mammalian cells or from mammalian viruses (e.g., the adenovirus late promoter or the vaccine virus 7.5K promoter). DNA encoding proteins to be assayed (i.e. sEH) can be transiently or stably expressed in the cell lines by several methods known in the art, such as, calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed. In addition native cell lines that naturally carry and express the nucleic acid sequences for the target protein may be used.

Typically, the test substance may be selected from the group consisting of peptides, peptidomimetics, small organic molecules, antibodies, aptamers or nucleic acids. For example the test substance according to the invention may be selected from a library of compounds previously synthesized, or a library of compounds for which the structure is determined in a database, or from a library of compounds that have been synthesized de novo. In a particular embodiment, the test substance may be selected form small organic molecules. As used herein, the term "small organic molecule" refers to a molecule of size comparable to those organic molecules generally sued in pharmaceuticals. The term excludes biological macromolecules (e.g.; proteins, nucleic acids, etc.); preferred small organic molecules range in size up to 2000 Da, and most preferably up to about 1000 Da.

The screening methods of the invention are very simple. It can be performed with a large number of test substances, serially or in parallel. The method can be readily adapted to robotics. For example, the above assays may be performed using high throughput screening techniques for identifying test substances for developing drugs that may be useful to the treatment or prevention of an inflammatory bowel disease. High throughput screening techniques may be carried out using multi-well plates (e.g., 96-, 389-, or 1536-well plates), in order to carry out multiple assays using an automated robotic system. Thus, large libraries of test substances may be assayed in a highly efficient manner A preferred strategy for identifying test substances starts with cultured cells transfected with a reporter gene fused to the promoter of any gene that is activated by the stress response pathway. More particularly, stably-transfected cells growing in wells of micro-titer plates (96 well or 384 well) can be adapted to high through-put screening of libraries of compounds. Compounds in the library will be applied one at a time in an automated fashion to the wells of the microtitre dishes containing the transgenic cells described above. Once the test substances which activate one of the target genes are identified, it is preferable to then determine their site of action in the Integrated Stress Response pathway. It is particularly useful to define the site of action for the development of more refined assays for in order to optimize the target substance.

In some embodiments, the test substances that have been positively selected may be subjected to further selection steps in view of further assaying its properties in in vitro assays such as described in the EXAMPLES of the present specification or in an animal model organism, such as a rodent animal model system, for the desired therapeutic activity prior to use in humans.

The invention will be further illustrated by the following figures and examples. However, these examples and figures should not be interpreted in any way as limiting the scope of the present invention.

FIGURES

FIG. 1: Inhibition of the sEH phosphatase domain with N-acetyl-S-farnesyl-L-cysteine (AFC) dose-dependently reduces the calcium content of rat aortas cultured in procalcifying conditions (inorganic phosphate; Pi=3.8 mM) during 7 days.

Figure 2:
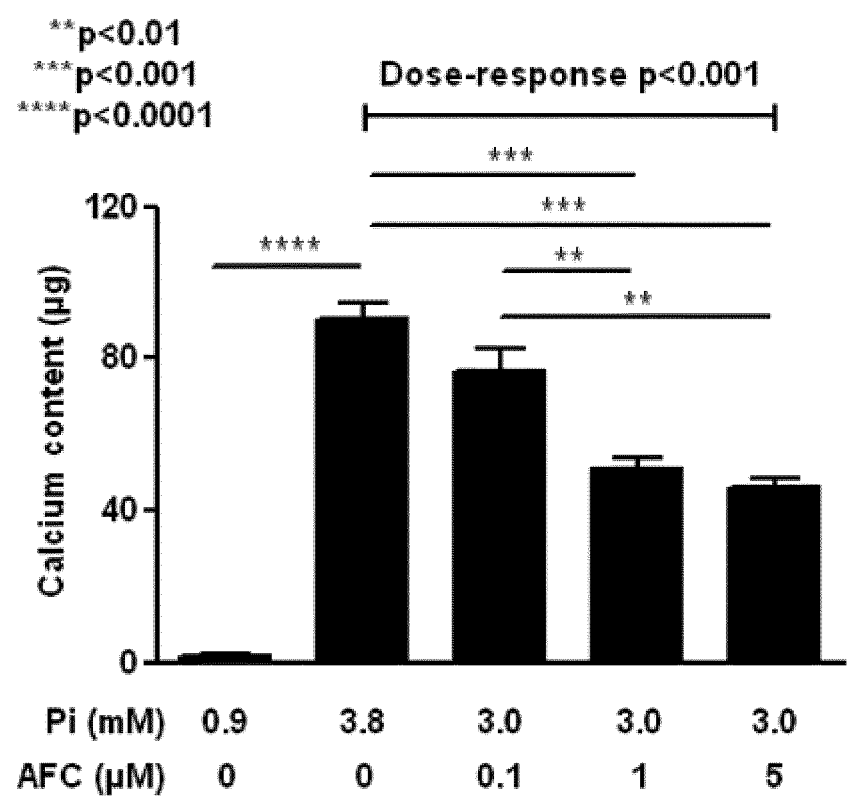

FIG. 2: Inhibition of the sEH phosphatase domain with N-acetyl-S-farnesyl-L-cysteine (AFC) dose-dependently reduces the calcium content of valvular interstitial cells cultured in procalcifying conditions (inorganic phosphate; Pi=3 mM) during 14 days.

Figure 3:
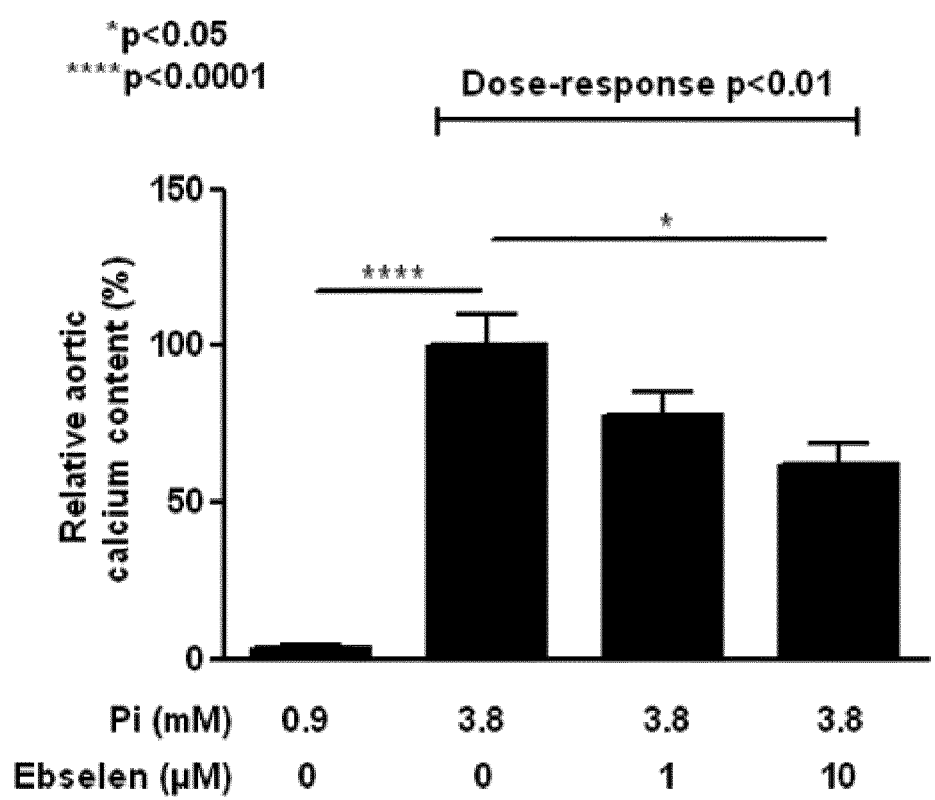

FIG. 3: Inhibition of the sEH phosphatase domain with ebselen dose-dependently reduces the calcium content of aortic rings cultured in procalcifying conditions (inorganic phosphate; Pi=3.8 mM) during 7 days.

Figure 4:
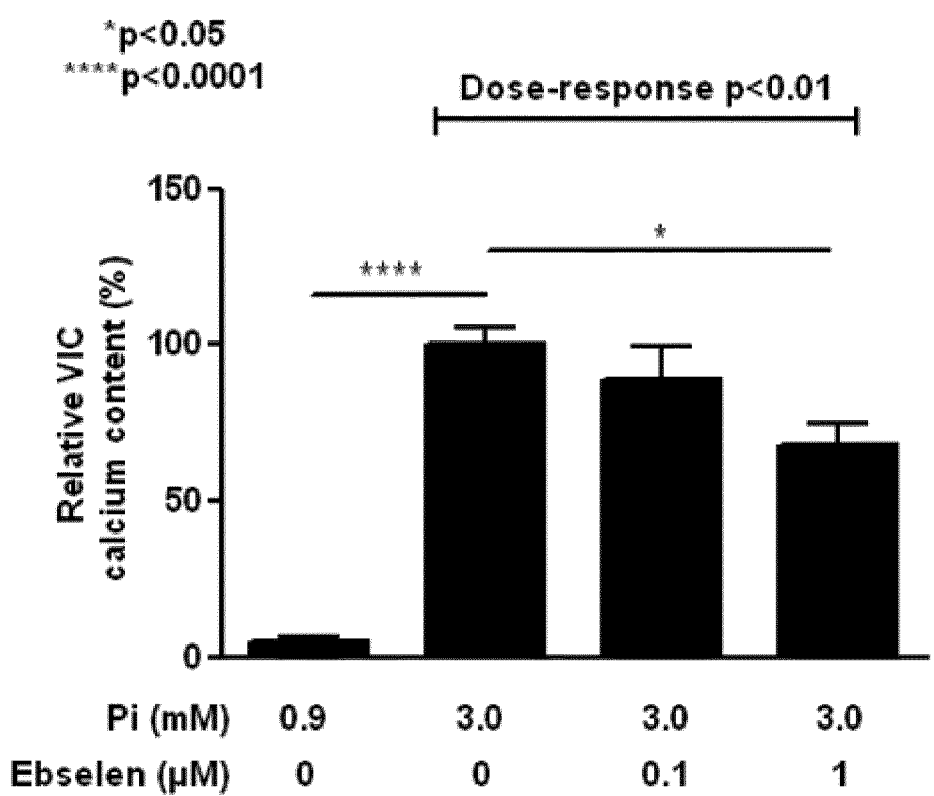

FIG. 4: Inhibition of the sEH phosphatase domain with ebselen dose-dependently reduces the calcium content of valvular interstitial cells cultured in procalcifying conditions (inorganic phosphate; Pi=3 mM) during 10 days.

EXAMPLE 1 (DATA NOT SHOWN)

Introduction: Notably expressed in the cardiovascular system either by endothelial, vascular smooth muscle and cardiac cells, soluble epoxide hydrolase (sEH) is a bifunctional enzyme which contributes to the regulation of the endothelial function and maintain of cardiovascular homeostasis. It is hypothesized that the enhanced cardiovascular calcification could be related to a procalcifying effect of sEH phosphatase.

Aim: In this work we assessed ex vivo the role of the sEH hydrolase domain in vascular calcification.

Materials and methods: Rat aortic rings were cultured in procalcifying conditions using inorganic phosphate (Pi: 3.8 mM) for 7 days. Trans-4-(4-(3-adamantan-1-yl-ureido)-cyclohexyloxy)-benzoic acid (t-AUCB)—a potent and specific inhibitor of sEH hydrolase—was added at concentrations, ranging from 0.1 to 10 µM (n=6-16 per group). Rat aortic calcium content was determined using a calcium colorimetric assay with O-Cresolphthalein.

Results: Aortic calcium content was significantly and dose-dependently increased by the inhibition of the phosphatase domain with t-AUCB (Pi: 100±9%; 0.1 µM: 110±9%; 1 µM: 128±15%; 10 µM: 141±16%). Alizarin Red and VonKossa histochemical staining confirmed these results.

Conclusion: These results demonstrate that the inhibition of the hydrolase domain of sEH increases the aortic calcification.

EXAMPLE 2 (FIG. 1)

Introduction: Notably expressed in the cardiovascular system either by endothelial, vascular smooth muscle and cardiac cells, soluble epoxide hydrolase (sEH) is a bifunctional enzyme which contributes to the regulation of the endothelial function and maintain of cardiovascular homeostasis. Aside from its hydrolase activity, sEH also possesses a phosphatase domain whose function has been poorly investigated.

Aim: In this work we assessed ex vivo the role of the sEH phosphatase domain in vascular calcification.

Materials and methods: Rat aortic rings were cultured in procalcifying conditions using inorganic phosphate (Pi: 3.8 mM) for 7 days. N-acetyl-S-farnesyl-L-cysteine (AFC)—sEH phosphatase domain inhibitor—was added at concentrations, ranging from 0.1 to 10 µM (n=4-21 per group). Rat aortic calcium content was determined using a calcium colorimetric assay with O-Cresolphthalein.

Results: Aortic calcium content was significantly and dose-dependently decreased by the inhibition of the phosphatase domain with AFC (Pi: 100±6.9%; Pi+AFC 0.1 µM: 83.6±9.1%; Pi+AFC 1 µM: 74.2±2.9%; Pi+AFC 10 µM: 54.5±12%). Alizarin Red and VonKossa histochemical staining confirmed these results.

Conclusion: These results demonstrate that the inhibition of the phosphatase domain of sEH may represent a new pharmacological target in the prevention of vascular calcification.

EXAMPLE 3 (FIG. 2)

Introduction: Notably expressed in the cardiovascular system either by endothelial, vascular smooth muscle and cardiac cells, soluble epoxide hydrolase (sEH) is a bifunctional enzyme which contributes to the regulation of the endothelial function and maintain of cardiovascular homeostasis. Aside from its hydrolase activity, sEH also possesses a phosphatase domain whose function has been poorly investigated.

Aim: In this work we assessed in vitro the role of the sEH phosphatase domain in valvular calcification.

Materials and methods: Human valvular interstitial cells (VICs) were cultured in procalcifying conditions using inorganic phosphate (Pi: 3 mM) for 14 days. N-acetyl-S-farnesyl-L-cysteine (AFC)—sEH phosphatase domain inhibitor—was added at concentrations, ranging from 0.1 to 5 µM (n=5-6 per group). VICs aortic calcium content was determined using a calcium colorimetric assay with O-Cresolphthalein.

Results: VICs calcium content was significantly and dose-dependently decreased by the inhibition of the phosphatase domain with AFC (mean±SEM; Pi: 90.3±4.6 µg; Pi+AFC 0.1 µM: 76.7±5.7 µg; Pi+AFC 1 µM: 51.1±2.9 µg; Pi+AFC 5 µM: 45.8±2 µg). Alizarin Red staining confirmed these results.

Conclusion: These results demonstrate that the inhibition of the phosphatase domain of sEH may represent a new pharmacological target in the prevention of valvular calcification.

EXAMPLE 4 (FIG. 3)

Introduction: Notably expressed in the cardiovascular system either by endothelial, vascular smooth muscle and cardiac cells, soluble epoxide hydrolase (sEH) is a bifunctional enzyme which contributes to the regulation of the endothelial function and maintain of cardiovascular homeostasis. Aside from its hydrolase activity, sEH also possesses a phosphatase domain whose function has been poorly investigated.

Aim: In this work we assessed ex vivo the role of the sEH phosphatase domain in vascular calcification.

Materials and methods: Rat aortic rings were cultured in procalcifying conditions using inorganic phosphate (Pi: 3.8 mM) for 7 days in absence and in presence of ebselen at a concentration of 1 and 10 µM (n=6-8 per group).

Results: Relative aortic calcium content was significantly and dose-dependently decreased by the inhibition of the phosphatase domain with ebselen (Pi: 100±10%; Pi+ebselen 1 µM: 77±8%; Pi+ebselen 10 µM: 62±7%).

Conclusion: These results demonstrate that the inhibition of the phosphatase domain of sEH may represent a new pharmacological target in the prevention of valvular calcification.

EXAMPLE 5 (FIG. 4)

Introduction: Notably expressed in the cardiovascular system either by endothelial, vascular smooth muscle and cardiac cells, soluble epoxide hydrolase (sEH) is a bifunctional enzyme which contributes to the regulation of the endothelial function and maintain of cardiovascular homeostasis. Aside from its hydrolase activity, sEH also possesses a phosphatase domain whose function has been poorly investigated.

Aim: In this work we assessed in vitro the role of the sEH phosphatase domain in valvular calcification.

Materials and methods: Human valvular interstitial cells (VICs) were cultured in procalcifying conditions using inorganic phosphate (Pi: 3 mM) for 10 days. Ebselen—sEH phosphatase domain inhibitor—was added at the concentrations of 0.1 and 1 µM (n=4 per group). VICs aortic calcium content was determined using a calcium colorimetric assay with O-Cresolphthalein.

Results: VICs calcium content was significantly and dose-dependently decreased by the inhibition of the phosphatase domain with ebselen (mean±SEM; Pi: 100±5.9%; Pi+ebselen 0.1 µM: 88.8±11%; Pi+ebselen 1 µM: 67.6±7.2%).

Conclusion: These results demonstrate that the inhibition of the phosphatase domain of sEH may represent a new pharmacological target in the prevention of valvular calcification.

REFERENCES

Throughout this application, various references describe the state of the art to which this invention pertains. The disclosures of these references are hereby incorporated by reference into the present disclosure.

The invention claimed is:

1. A method of treating cardiovascular calcification in a subject in need thereof comprising administering to the subject a therapeutically effective amount of an inhibitor of phosphatase activity of soluble epoxide hydrolase, wherein the inhibitor of phosphatase activity of soluble epoxide hydrolase is N-acetyl-S-farnesyl-Lcysteine (AFC) or ebselen.

2. The method of claim 1 wherein the cardiovascular calcification is valvular or vascular calcification.

3. The method of claim 1 wherein the subject is elderly and/or has a mineral imbalance disorder.

4. An in vitro method for screening a plurality of test substances to identity those which are useful for the treatment of cardiovascular calcification in a subject in need thereof comprising i) testing each of the test substances for its ability to inhibit the phosphatase activity of soluble epoxide hydrolase and ii) identifying a test substance which inhibits said phosphatase activity as useful for treating cardiovascular calcification in a subject in need thereof.

5. The method of claim 3, wherein the mineral imbalance disorder is associated with severe renal failure in a subject on hemodialysis, a hemodialysis arteriovenous (AV) graft/shunt, a vein graft, a vascular anastomosis, diabetes, Paget's disease, rheumatoid arthritis, osteoporosis or osteoarthritis.

* * * * *